(12) United States Patent
Darsale

(10) Patent No.: US 8,920,853 B2
(45) Date of Patent: Dec. 30, 2014

(54) NOURISHING OIL COMPOSITION, POMADE, COMPOSITION FOR PROMOTING HAIR GROWTH, SHAMPOO, CONDITIONER, HAIR ROOT STIMULATOR, AND METHODS FOR MAKING AND USING THE SAME

(75) Inventor: Cynthia Sayblee Darsale, Miami, FL (US)

(73) Assignee: Sayblee Handmade Natural Hair Care, LLC, Miami, FL (US)

( * ) Notice: Subject to any disclaimer, the term of this patent is extended or adjusted under 35 U.S.C. 154(b) by 0 days.

(21) Appl. No.: 13/484,267

(22) Filed: May 30, 2012

(65) Prior Publication Data
US 2013/0323333 A1 Dec. 5, 2013

(51) Int. Cl.
*A01N 65/00* (2009.01)

(52) U.S. Cl.
USPC ........................................ 424/725

(58) Field of Classification Search
CPC ...... A61K 36/00; A61K 36/58; A61K 36/886
USPC ................... 424/725, 744, 768, 776
See application file for complete search history.

(56) References Cited

U.S. PATENT DOCUMENTS

2005/0069516 A1\* 3/2005 Hornby et al. ................. 424/74

\* cited by examiner

*Primary Examiner* — Michael Meller
(74) *Attorney, Agent, or Firm* — Assouline & Berlowe, P.A.; Loren Donald Pearson

(57) ABSTRACT

Compositions for promoting hair growth can be formed using food related oils. The food related oils include meadowfoam seed oil, neem oil, sesame oil, camelina, flaxeed oil, and tamanu oil. The oil can be combined with lime peel essential oil and/or aloe vera to create various products. The products in an oil for treating the hair and scalp, a treatment for damaged hair and scalp, shampoo, conditioner, pomade and hair root stimulant. A method for making each product is described. In addition, a method for using each product is described.

7 Claims, No Drawings

NOURISHING OIL COMPOSITION, POMADE, COMPOSITION FOR PROMOTING HAIR GROWTH, SHAMPOO, CONDITIONER, HAIR ROOT STIMULATOR, AND METHODS FOR MAKING AND USING THE SAME

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The invention relates to compositions for treating hair.

2. Description of the Related Art

Many clients of hair salons have damaged hair. Permanent hair treatments dry the customer's hair and make the hair brittle. The damage is caused by over processing.

A number of components used in the invention, exist and are commercially available, often for food and seasoning related purposes.

Aloe vera gel is available in a form that has been processed from the plant. The gel is made from aloe vera leaf juice and glycerin.

Grape seed extracts are industrial derivatives from whole grape seeds.

Camelina sativa is usually known in English as camelina.

Cetostearyl alcohol, cetearyl alcohol or cetylstearyl alcohol is a mixture of fatty alcohols, consisting predominantly of cetyl and stearyl alcohols and is classified as a fatty alcohol. It is used as an emulsion stabilizer, opacifying agent, and foam boosting surfactant, as well as an aqueous and nonaqueous viscosity-increasing agent. It imparts an emollient feel to the skin and can be used in water-in-oil emulsions, oil-in-water emulsions, and anhydrous formulations. It is commonly used in hair conditioners and other hair products.

Decyl glucoside is a mild non-ionic surfactant used in cosmetic formularies including baby shampoo and in products for individuals with a sensitive skin. Many natural personal care companies use this cleanser because it is plant-derived, biodegradable, and gentle for all hair types.

Glycerol (or glycerine, glycerin) is a simple polyol compound. It is a colorless, odorless, viscous liquid that is widely used in pharmaceutical formulations. Glycerol has three hydroxyl groups that are responsible for its solubility in water and its hygroscopic nature. The glycerol backbone is central to all lipids known as triglycerides. Glycerol is sweet-tasting and of low toxicity.

Guar gum, also called guaran, is a galactomannan. Guar gum is typically produced as a free-flowing, pale, off-white-colored, coarse to fine ground powder.

Lavender oil is an essential oil obtained by distillation from the flower spikes of certain species of lavender.

Lime Peel Essential Oil is made cold-pressing lime, *Citrus aurantifolia*, peels.

Linseed oil, also known as flaxseed oil, is a clear to yellowish oil obtained from the dried ripe seeds of the flax plant (*Linum usitatissimum*, Linaceae). The oil is obtained by cold pressing, sometimes followed by solvent extraction.

Meadowfoam seed oil is an edible seed oil, extracted from the seeds of *Limnanthes alba* (meadowfoam). The seeds contain 20-30% oil. Meadowfoam oil is widely used in cosmetic and hair-care applications due to its stability, lubricity and ability to stay on the skin.

Neem oil is a vegetable oil pressed from the fruits and seeds of the neem (*Azadirachta indica*), an evergreen tree which is endemic to the Indian subcontinent and has been introduced to many other areas in the tropics.

Rosemary antioxidant extract is produced from rosemary. Rosemary, *Rosmarinus officinalis*, is a woody, perennial herb with fragrant, evergreen, needle-like leaves and white, pink, purple or blue flowers. To create the antioxidant, whole fresh Rosemary leaf is put through a supercritical $CO_2$ extraction process. Rosemary antioxidant extract is used as a natural preservative.

Sage oil is the essential oil made from the culinary herb sage, *Salvia officinalis*.

Sesame oil (also known as gingelly oil or til oil) is an edible vegetable oil derived from sesame seeds.

Shea butter is a slightly yellowish or ivory-colored fat extracted from the nut of the African shea tree (*Vitellaria paradoxa*).

Stearic acid is the saturated fatty acid with an 18 carbon chain.

Sunflower oil is the non-volatile oil expressed from sunflower (*Helianthus annuus*) seeds. Sunflower oil is commonly used in food as a frying oil, and in cosmetic formulations as an emollient.

Sweet almond extract is comprised of sweet almond oil mixed with water and alcohol.

Tamanu oil (also called foraha or doomba oil) is pressed from nuts of the *Calophyllum tacamahaca* (or ati) tree. The nuts yield 70-75% of the greenish-yellow inedible oil. Commercial exploitation of tamanu oil is predominantly for skin care.

*Cananga odorata*, commonly called ylang-ylang, is a tree valued for its perfume. Ylang ylang essential oil derived from the flowers is used in aromatherapy.

Xanthan gum is a polysaccharide and is commonly used as a food thickening agent.

Wheat germ is the reproductive part of a wheat seed

BRIEF SUMMARY OF THE INVENTION

An object of the invention is to provide compositions for hair, methods of making the composition, and methods of using the compositions that overcome the disadvantages of the compositions and methods of this general type and of the prior art.

With the foregoing and other objects in view there is provided, in accordance with the invention, compositions for promoting growth of healthy hair are taught. The composition improves the shine of hair.

Using fresh components has been found to improve the efficacy of the composition.

An object of the opposition is to provide a composition that does not include sulfates, mineral oil, gluten, paraffin, parabens, phthalates, propylene glycol, artificial fragrances, DEA, and artificial coloring.

An object of the invention is to provide compositions that do not require animal testing.

A further object of the invention is to provide a product that can be used on all hair type including braiding, twist, and cornrows.

A further object of the invention is to provide products using the active ingredients of the composition. The products include the following:

Nourishing Oil Composition
Pomade
Composition for Promoting Hair Growth
Shampoo
Conditioner
Hair Root Stimulator Composition The invention encompasses a nourishing oil composition for promoting hair growth. The composition includes at least two oils. At least one of the oils is meadowfoam seed oil, neem oil, sesame oil, camelina, flaxseed oil, or tamanu oil. The second oil can be lime peel essential oil. When the second oil is lime peel essential oil, the lime peel essential oil forms less than thirty percent of a volume of the nourishing oil.

The invention encompasses a pomade composition for styling hair and promoting hair growth. The pomade includes an oil, aloe vera gel, and a softening agent. The oil can be meadowfoam seed oil, neem oil, sesame oil, camelina, flaxseed oil, or tamanu oil. The aloe vera can be from any source including aloe vera gel. The pomade includes a softening agent. Potential softening agents include shea butter and stearic acid.

The invention encompasses a composition for promoting hair growth that includes aloe vera and an oil selected from the group consisting of meadowfoam seed oil, neem oil, sesame oil, camelina, flaxseed oil, and tamanu oil. The aloe vera can form 30-62% by volume of the composition.

The invention encompasses a method for promoting hair growth. The method includes applying the composition for promoting hair growth to the hair. The composition is allowed to remain on the hair for at least twenty minutes. The treated hair can be heated using a hood dryer, steam cap, or similar device. After at least twenty minutes have passed, the composition is rinsed from the hair.

The invention encompasses a shampoo for promoting hair growth. The shampoo includes aloe vera gel and an oil. The oil can be meadowfoam seed oil, neem oil, sesame oil, camelina, flaxseed oil, or tamanu oil. The aloe vera gel can form up to 7% of the shampoo by volume.

The invention encompasses a hair conditioner for promoting hair growth that includes aloe vera and meadowfoam seed oil.

The invention encompasses a hair root stimulator composition for stimulating and healing hair roots. The composition includes an oil. The oil can be ylang ylang, meadowfoam seed oil, camelina oil, neem oil, flaxseed oil, or a composition thereof.

Other features that are considered as characteristic for the invention are set forth in the appended claims.

Although the invention is illustrated and described herein as embodied in a nourishing oil composition, pomade, composition for promoting hair growth, shampoo, and methods for making and using the nourishing oil composition, pomade, composition for promoting hair growth, and shampoo, the invention should not be limited to the details shown in those embodiments because various modifications and structural changes may be made without departing from the spirit of the invention while remaining within the scope and range of equivalents of the claims.

The construction and method of operation of the invention and additional objects and advantages of the invention is best understood from the following description of specific embodiments when read in connection with the accompanying examples.

BRIEF DESCRIPTION OF THE SEVERAL VIEWS OF THE DRAWING

Not applicable.

DETAILED DESCRIPTION OF THE INVENTION

Nourishing Oil Composition

The invention includes a nourishing oil composition for treating hair and scalp as well as a method for making the composition and a method of using the composition.

The nourishing oil composition provides a balance of natural herbs and essential oils that are blended to promote hair growth, to moisturize dry scalp, and prevent dandruff. The composition can be applied to all types of hair styles: for example, cornrows, two-strand twists, plaits, combtwists, and weaves. The nourishing oil provides moisture and improves shine without making hair greasy. When used correctly on styled hair, cornrows, twists, plaits, and weaves are more easily unraveled. The nourishing oil composition can be used on all types of hair for flat ironing or pressing. The nourishing oil composition does not require animal testing. The nourishing oil composition includes no synthetic ingredients.

Nourishing Oil Composition

An embodiment of a nourishing oil composition for hair and scalp is formed from the following components. The efficacy of the following nourishing oil composition was less than other embodiments. The amount of lime peel oil in the composition was too great and affected the hair and scalp.

| COMPONENT | VOLUME | VOL % |
|---|---|---|
| Tamanu oil | 1 TBSP | 5 |
| Neem oil | 1 TBSP | 5 |
| Rosemary antioxidant extract | 3 TBSP | 15 |
| Lime peel essential oil | 6 TBSP | 30 |
| Sunflower oil | 2 TBSP | 10 |
| Camelina | 1 TBSP | 5 |
| Meadowfoam seed oil | 4 TBSP | 20 |
| Sesame oil | 2 TBSP | 10 |

Nourishing Oil Composition

A preferred embodiment of a nourishing oil composition is described below.

| INGREDIENT | VOLUME | VOLUME % |
|---|---|---|
| Tamanu oil | 1 TBSP | 3 |
| Neem oil | 1 TBSP | 3 |
| Rosemary anti-oxidant extract | 3 TBSP | 9 |
| Lime peel essential oil | 6 TBSP | 17 |
| Sunflower oil | 7 TBSP | 20 |
| Camelina | 1 TBSP | 3 |
| Meadowfoam seed oil | 14 TBSP | 40 |
| Sesame oil | 2 TBSP | 6 |

Nourishing Oil Composition

A preferred embodiment of nourishing oil for treating hair is described below.

| INGREDIENT | VOLUME | VOLUME % |
|---|---|---|
| Lime peel essential oil | 6 TBSP | 18 |
| Tamanu oil | 1 TBSP | 3 |
| Meadowfoam seed oil | 12 TBSP | 36 |
| Sunflower oil | 7 TBSP | 21 |
| Camelina | 1 TBSP | 3 |
| Neem oil | 1 TBSP | 3 |
| Rosemary antioxidant extract | 3 TBSP | 9 |
| Sesame oil | 2 TBSP | 6 |

A preferred embodiment of nourishing oil for treating hair is described below.

| INGREDIENT | VOLUME | VOLUME % |
|---|---|---|
| Lime peel essential oil | 6 TBSP | 18 |
| Tamanu oil | 1 TBSP | 3 |
| Meadowfoam seed oil | 14 TBSP | 40 |
| Sunflower oil | 7 TBSP | 20 |
| Camelina | 1 TBSP | 3 |
| Neem oil | 1 TBSP | 3 |
| Rosemary antioxidant extract | 3 TBSP | 9 |
| Sesame oil | 2 TBSP | 6 |

Method of Making Nourishing Oil Composition

A preferred method of making the nourishing oil composition follows. The oils are measured and mixed, with the exception of the lime peel essential oil. The mixture is then heated to no more than ninety-four degrees centigrade (<94° C.) for up to five minutes. Next, the lime peel essential oil is added. Next, the mixture is mixed while being heated to no more than ninety-four degrees centigrade (<94° C.) for up to five additional minutes.

Method of Using the Nourishing Oil Composition

A preferred embodiment of a method for using the nourishing oil composition follows. The first step is applying the nourishing oil composition, preferably by spraying, to the hair, directly to the shaft of the hair and the scalp. The nourishing oil is massaged gently into the hair. The hair is styled as desired. Alternatively, the nourishing oil composition is sprayed onto the scalp after styling the hair.

The nourishing oil composition is preferably applied once to twice per week depending on the condition of the hair.

Pomade

A preferred embodiment of the invention is a pomade. The pomade is a selective blend of natural and organic oils formulated to redeem very dry, brittle, limp hair. The hair can be coarse, medium, or fine. The pomade returns hair to a healthy, moist, and shiny state without a greasy buildup. The pomade can be used with all kinds of styled hair including hair that is in cornrows, two-strand twists, plaits, combtwists, and weaves. The pomade softens and moistens hair.

Pomade Composition

A preferred embodiment of a pomade has the following composition.

| INGREDIENT | VOLUME | VOL % | MASS | WT % |
|---|---|---|---|---|
| Sesame oil | 1 TBSP | 4 | 0.7 oz | 5 |
| Sunflower oil | 1 TBSP | 4 | 0.7 oz | 5 |
| Sweet almond extract | 4 TBSP | 17 | 2.3 oz | 17 |
| Meadowfoam Seed oil | 2 TBSP | 8 | 1.1 oz | 8 |
| Rosemary antioxidant extract | 2 TBLSP | 8 | 1.1 oz | 8 |
| Aloe vera gel | 6 TBSP | 26 | 2.7 oz | 20 |
| Shea butter | 5 TBSP | 21 | 2.9 oz | 22 |
| Stearic acid | 2 TBSP | 8 | 1.7 oz | 13 |
| Xanthan gum | 1 tsp | 1 | 0.2 oz | 1 |

Method for Preparing the Pomade

The following is a preferred embodiment of a method to prepare the pomade. First, the stearic acid and shea butter are heated until dissolved. Next, the other oils are added. Next, the aloe vera gel is heated separately. The warm aloe vera gel and oils are then mixed. Xanthan gum is admixed until the mixture is creamy.

Method for Using the Pomade

The following is a preferred embodiment of a method to use the pomade. To use the pomade, an amount sufficient to lightly coat the shaft of the hair is applied. Then, the hair is styled as desired. For daily maintenance of the hair and scalp, the nourishing oil composition can be applied to the hair after styling.

Composition for Promoting Hair Growth

The composition for treating damaged hair and scalp is a unique blend of essential oils and plant extracts. The composition is formulated to promote hair growth. The ingredients penetrate and remain on the hair follicles. The composition stimulates treated hair follicles to repair damage. In addition, the composition prevents further damage to the hair by protecting the following. The composition restores damages hair shafts to normal. As a result, treated hair feels soft, shines, and is easier to manage. Damaged hair that has been treated becomes healthy.

Composition for Promoting Hair Growth

A preferred embodiment for a composition for treating hair is described below.

| INGREDIENT | VOLUME | VOL % |
|---|---|---|
| Sage oil | 8 drops | 0.1 |
| Lyang lyang | 8 drops | 0.1 |
| Flaxseed oil | 1 TBSP | 5 |
| Camelina | 0.6 | 3 |
| Sunflower oil | 0.6 | 3 |
| Sesame oil | 0.6 | 3 |
| Tamanu oil | 0.7 | 3 |
| Rosemary antioxidant extract | 1.1 | 5 |
| Neem oil | 0.7 | 3 |
| Lavender oil | 1.7 | 8 |
| Xanthan Gum | 0.4 | 2 |
| Aloe vera gel | 12 | 60 |
| Meadow foam seed oil | 0.6 | 3 |

Composition for Promoting Hair Growth

The oil described in the table below was based on the oil described in the second following table.

| INGREDIENT | VOLUME | VOL % |
|---|---|---|
| Oil | 3-4 TBSP | 30-50 |
| Aloe vera gel | 3-4 TBSP | 30-50 |
| Lime peel oil | 2 TBSP | 20-25 |

A nourishing oil composition for treating hair and scalp and for preparing further compositions is described below.

| INGREDIENT | VOLUME | VOL % |
|---|---|---|
| Sage oil | 7 Drops | 0.05 |
| Ylang-ylang | 7 Drops | 0.05 |
| Flaxseed oil | 1 TBSP | 3 |
| Camelina | 1 TBSP | 3 |
| Sunflower oil | 1 TBSP | 3 |
| Sesame oil | 1 TBSP | 3 |
| Tamanu oil | 1 TBSP | 3 |
| Rosemary antioxidant extract | 3 TBSP | 8 |

-continued

| INGREDIENT | VOLUME | VOL % |
|---|---|---|
| Neem oil | 1 TBSP | 3 |
| Lavender oil | 3 TBSP | 8 |
| Xanthan gum | 4 TBSP | 11 |
| Aloe vera gel | 20 TBSP | 54 |
| Meadowfoam seed oil | 1 TBSP | 3 |

Composition for Promoting Hair Growth

An alternative embodiment of a composition for promoting hair growth follows.

| COMPONENT | VOLUME | VOL % |
|---|---|---|
| Sage oil | 8 drops | 0.1 |
| Lyang lyang | 8 drops | 0.1 |
| Flaxseed oil | 1 TBSP | 3 |
| Camelina | 1 TBSP | 3 |
| Sunflower oil | 1 TBSP | 3 |
| Sesame oil | 1 TBSP | 3 |
| Tamanu oil | 1 TBSP | 3 |
| Rosemary antioxidant extract | 2 TBSP | 6 |
| Neem oil | 1 TBSP | 3 |
| Lavender oil | 3 TBSP | 9 |
| Xanthan gum | 0.5 TBSP | 2 |
| Aloe vera gel | 20 TBSP | 62 |
| Meadowfoam seed oil | 1 TBSP | 3 |

Method for Preparing the Composition for Promoting Hair GROWTH

A preferred embodiment of a method for preparing the composition for promoting hair growth follows. To mix the composition, first the oils are mixed together. Next, the aloe vera gel is mixed separately. While still mixing the aloe vera gel, the oil is added and mixed. Next, xanthan gum is admixed until the mixture is thick and creamy. The amount of xanthan gum is adjusted to control the thickness of the composition.

Preferably, the composition is not heated when being prepared.

Method for Using the Composition for Promoting Hair Growth

A preferred method of using the composition to promote hair growth follows. First, after shampooing one's hair, the hair is towel dried, leaving the hair damp. Next, the composition is added to the scalp and hair shaft. The amount depends on the thickness of the hair. After adding, the scalp is massaged vigorously to stimulate the hair follicles. The head with the composition is placed under a hood dryer for twenty (20) minutes. Alternatively, if a hood dryer is not available, one can place a cap over the treated hair for thirty minutes. Another alternative is to place a steam cap over the treated hair for twenty minutes. Next, after allowing the composition to treat the hair, the composition is rinsed from the hair. The hair is styled as usual. The pomade is preferably used to style the hair. The nourishing oil composition is added to the scalp after the hair is styled.

Shampoo

A preferred embodiment of a shampoo for washing hair is described below.

| COMPONENT | VOLUME | VOL % |
|---|---|---|
| Decyl glucoside | 37 TBSP | 32 |
| Aloe vera gel | 8 TBSP | 7 |
| Glycerin | 8 TBSP | 7 |
| Sage oil | 40 drops | 0.4 |
| Lime peel essential oil | 4 TBSP | 3 |
| Meadowfoam seed oil | 2 TBSP | 2 |
| Sunflower oil | 4 TBSP | 3 |
| Camelina | 2 TBSP | 2 |
| Sweet almond extract | 2 TBSP | 2 |
| Guar gum | 6 TBSP | 5 |
| Water | 40 TBSP | 34 |
| Wheat germ | 2 TBSP | 2 |
| Grapefruit seed extract | 2 TBSP | 2 |

Method of Preparing Shampoo

A preferred embodiment of making the shampoo is the following. A portion of the water is first warmed and then boiled. Once boiling, the aloe vera gel and glycerin are added. The aloe vera gel and glycerin are mixed until completely dissolved. The mixture is then removed from heat while continuing to mix the mixture. Next, the oils are added. Next, in a separate vessel, the guar gum is mixed with the remaining water. The mixture is stirred until smooth. The guar gum/water mixture is then mixed with the first mixture to complete the shampoo.

Conditioner for Hair

What does it do

The conditioner for hair is a selective blend of natural herbs and essential oils formulated to provide moisture, shine, and softness, and to detangle the hair. The conditioner infuses the hair with vitamins and proteins. The conditioner rebuilds very dry hair by adding moisture to leave the hair easy to manage.

Conditioner for Hair Composition

A preferred embodiment of a conditioner for hair follows.

| COMPONENT | WEIGHT | VOLUME |
|---|---|---|
| Water | 4 oz | 21 TBSP |
| Aloe vera extract, liquid | 2 oz | |
| Cetearyl alcohol | 2.6 oz | 6 TBSP |
| Aloe vera gel | 2.9 oz | |
| Sweet almond oil | 2.4 oz | |
| Sage | 0.1 oz | |
| Grapefruit seed extract | 16 oz | 2 TBSP |
| Meadowfoam seed oil | 1.2 oz | 1 TBSP |
| Glycerin | 2.8 oz | |
| Stearic acid | 1.4 | 2 TBSP |
| Lime peel essential oil | 0.6 oz | 2 TBSP |
| Vitamin B-5 | | 4 TBSP |

Method for Making Conditioner

A preferred embodiment for making a conditioner for hair follows. The first step involves placing the water in a vessel. Next, the vessel is heated to bring the water to a boil. In a separate vessel, the oils are mixed along with the vitamin B-5. Next, the cetearyl alcohol and stearic acid are added to the vessel holding the oils. Finally, the oil mixture is mixed with the hot water. The mixture is blended until creamy.

Method for Using the Conditioner

A preferred embodiment for using the conditioner follows. After shampooing the hair, preferably with shampoo specified in this application, a desired amount of conditioner is applied to the hair. Next, the conditioner is allowed to stay on the hair for about three to five minutes. Next, the conditioner is rinsed completely from the hair. Next, the hair is styled as usual with the nourishing oil composition, roots stimulator, and/or pomade.

Hair Root Stimulator Composition

A root stimulator composition is a selective blend of natural and essential oil formulated to stimulate and revitalize the hair follicles to help promote hair growth.

Root Stimulator Composition

A preferred embodiment of a root stimulator composition follows.

| COMPONENT | VOLUME | VOL % |
|---|---|---|
| Ylang ylang | 15 drops | 0.31 |
| Sage oil | 15 drops | 0.31 |
| Sesame oil | 2 TBSP | 13 |
| Sunflower oil | 2 TBSP | 13 |
| Meadowfoam seed oil | 2 TBSP | 13 |
| camelina | 1 TBSP | 6 |
| Neem oil | 2 TBSP | 13 |
| Flaxseed oil | 1 TBSP | 6 |
| Lavender oil | 2 TBSP | 13 |
| Rosemary antioxidant extract | 2 TBSP | 13 |
| Cetearyl alcohol | 2 TBSP | 13 |

Method for Making Root Stimulator Composition

A preferred embodiment of a method of making root stimulator follows. The first is step is to heat a vessel. While heating, the cetearyl alcohol is added and allowed to melt. The cetearyl alcohol should be melted under low heat. Next, the camelina, neem, and flaxseed oil are added. The mixture is stirred for about five minutes. Next, the rosemary antioxidant extract, meadowfoam seed oil, sunflower oil, and sesame oil are added. The mixture is stirred for about five minutes. Next, the mixture is removed from the heat. Finally, the ylang ylang, sage oil, and lavender oil are added. The mixture is stirred until creamy and slightly thick.

Method for Using the Root Stimulator Composition

A preferred embodiment of a method for using the root stimulator composition follows. For stimulating effect, the hair is sectioned. Next, the root stimulator composition is added to the scalp. Next, the composition is massaged gently on the entire scalp including the temple area. The root stimulator composition should be applied one to three times a week depending on the condition of the scalp.

Because modifications, variations, and changes in detail can be made to the described preferred embodiments of the invention, it is intended that all matters in the foregoing description and described in the examples be interpreted as illustrative and not in a limiting sense. Thus, the scope of the invention should be determined by the appended claims and their legal equivalents.

What is claimed is:

1. A method for repairing damaged hair follicles in a human in need thereof, consisting essentially of:
    a) identifying a human with damaged hair follicles;
    b) providing a therapeutically effective amount of a composition for repairing damaged hair follicles, consisting essentially of therapeutically effective amounts of an aloe vera extract, lime peel essential oil, and an oil selected from the group consisting of meadowfoam seed oil, neem oil, sesame oil, camelina oil, flaxseed oil, and tamanu oil;
    c) applying the composition to the damaged hair follicles of the human;
    d) heating the damaged hair follicles with the composition applied thereto with a device for heating hair; and
    e) allowing said composition to remain on the damaged hair follicles of the human for at least twenty minutes to repair damaged hair follicles of the human.

2. The method of claim 1, wherein heat is applied to the hair when said composition is applied to the hair.

3. The method of claim 1, wherein after the at least 20 minutes, rinsing said composition from the damaged hair follicles of the human.

4. The method of claim 1, wherein said aloe vera extract forms 30-62% by volume of the composition.

5. The method of claim 1, wherein said device for heating hair is a steam cap.

6. The method of claim 1, wherein said device for heating hair is a hair dryer.

7. The method of claim 1, wherein said device for heating hair is a hood dryer.

* * * * *